United States Patent [19]
Duncan

[11] Patent Number: 6,131,443
[45] Date of Patent: Oct. 17, 2000

[54] CORROSION MONITOR

[76] Inventor: William P. Duncan, 31 Berkley Rd., Hopatcong, N.J. 07843

[21] Appl. No.: 09/366,601

[22] Filed: Aug. 4, 1999

[51] Int. Cl.⁷ ..................................................... F16K 37/00
[52] U.S. Cl. ................................................................ 73/86
[58] Field of Search ............................. 73/86, 7; 138/36; 340/605

[56] References Cited

U.S. PATENT DOCUMENTS

| | | | |
|---|---|---|---|
| 1,426,956 | 8/1922 | Case | 138/36 |
| 3,922,999 | 12/1975 | Meginnis | 138/36 |
| 5,253,674 | 10/1993 | Argyle et al. | 73/86 |

FOREIGN PATENT DOCUMENTS

| | | | |
|---|---|---|---|
| 45-31637 | 10/1970 | Japan | 73/86 |

*Primary Examiner*—Robert Raevis
*Attorney, Agent, or Firm*—Alfred C. Hill

[57] ABSTRACT

A self-contained, disposable corrosion monitor for a fluid containing system comprising a plug insertable into a fluid containing system, the plug indicating a preselected amount of loss of metal on an inner wall of the system due to corrosive action of the fluid on the inner solid monitoring wall of system. The plug includes a wall of the predetermined metal having a thickness equal to the preselected amount of loss and one surface exposed to the fluid when the plug is inserted into the fluid containing system at the same level as the inner wall of the system, an enclosed cavity associated with the other surface of the monitoring wall and a substance disposed within the enclosed cavity reacting with the fluid penetrating the monitoring wall to indicate when fluid has penetrated the monitoring wall and, hence, that the preselected amount of loss of the metal on the inner wall of the fluid containing system has occurred.

6 Claims, 1 Drawing Sheet

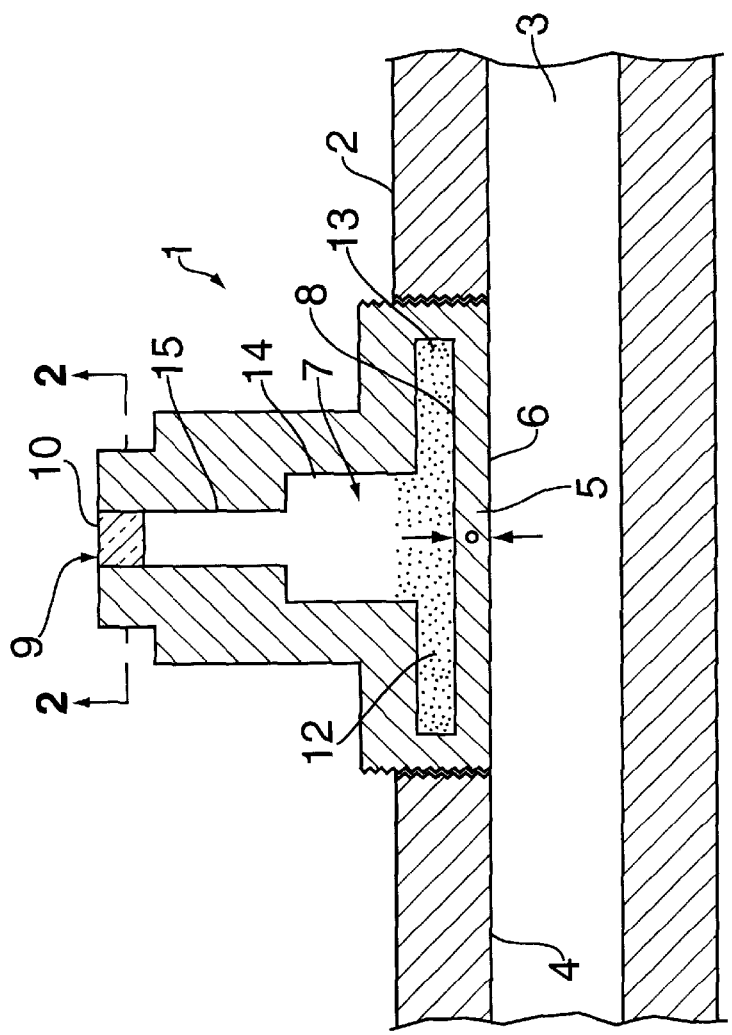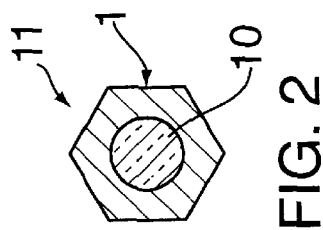

CORROSION MONITOR

BACKGROUND OF THE INVENTION

The present invention relates to corrosion monitoring devices and more particularly to a self contained, disposable corrosion monitor for a fluid containing system to indicate a preselected loss of a predetermined metal on an inner wall surface of the system due to the corrosive action of a fluid in the fluid containing system.

Failures of metal pipes, tanks and fluid enclosures due to the deterioration of their inner wall surfaces are all too common occurrences; currently causing over 10 billion dollars annually in replacement costs alone. While some corrosion induced metal failures may create a great and unexpected financial loss due to replacement cost, down time and water damage, the more severe failures of high temperature and high pressure pipes and vessels may result in explosion, extensive physical damage, severe injury and human casualty. Effective corrosion monitoring is therefore greatly desired from such a production, health, environmental, process reliability, economic and liability viewpoint.

Corrosion of metal surfaces is a continuous and generally non-stoppable electrochemical process which is well known and documented. Given sufficient time, metal failures are inevitable where fluids and metal meet and interact, and where at best, the negative physical effects of corrosion can only be minimized, not eliminated.

Due to the complex interaction of chemical, electrical and mechanical influences which determine the degree of activity of a corrosion environment, and the fact that such corrosion activity often widely varies at different locations within the same fluid environment, there is the need to monitor as many individual locations in a given piping system, tank, pressure vessel or reactor vessel as possible. The inability to monitor the corrosion activity at multiple locations within a piping system is frequently a cause of failure, since a single monitoring point, not representative of the corrosion in the entire piping system, may produce an erroneous prediction of surface life and surface failure.

Chemical and electrical corrosion inhibitors and other substances exist to help reduce corrosion and are often relied upon exclusively to safeguard piping and other metal components. The use of such corrosion inhibitors does not preclude the need for corrosion monitoring, however, since actual results of anti-corrosion agents vary widely, thereby making it necessary to regularly verify their efficiency and proper application.

A wide variation of corrosion monitors and procedures exist in the literature and in current use with the purpose of measuring the corrosive nature of a fluid or fluid stream against a specific metal surface. These devices may be mechanical, electrical or chemical in design and measuring instantaneous, average or accrued corrosion, and typically produce a corrosion rate measurement defined in mils per year (MPY).

Various types of currently available electronic instrumentation provide instantaneous, real time detail of the corrosion rate of MPY through the use of the insertion probes measuring changes in voltage, oxidation potential or other electro-chemical characteristics associated with a corrosion condition. Such devices fail to provide accumulated or total loss of metal in inches, require remote wiring to a main display instrument location, are sophisticated in design and, therefore, expensive to purchase and require regular maintenance, recalibration and supervision. Such devices, therefore, find limited actual field use, provide unsatisfactory corrosion monitoring coverage due to the limited number of sensors or probes installed and provide little benefit in all but the most critical of applications.

The most commonly used mechanical corrosion measuring device, termed a "corrosion coupon", consists of a thin flat bar of a specific composition metal (typically steel, brass, stainless steel or copper) having the approximate dimension of 1.75 in.×0.75 in.×0.125 in. One or more corrosion coupons are typically inserted in a by-pass flow assembly located external to the fluid system. This flow assembly routes a small volume of the fluid to be evaluated across the metal corrosion coupon surface. Under limited physical conditions permitting such use, corrosion coupons may be also inserted directly into a pipe or pressure vessel. The possibility of losing the coupon in the tank or circulating system generally precludes such use however.

Corrosion coupons are precisely preweighed in a laboratory prior to use, left within the flow assembly pipe or pressure vessel to naturally deteriorate over a given period of time (typically 60 to 180 days), and then removed for a follow-up laboratory analysis. Weight loss is measured, and a calculation made extrapolating the overall weight loss into a determination of MPY.

Ultrasonic testing is well recognized for providing extremely accurate remaining wall thickness measurements for any metal structure, but typically serves as a survey or an instantaneous measuring tool rather than a long term monitoring device. It has a disadvantage of being a temporary measurement instrument, is expensive, requires an experienced operator and careful analysis and manipulation of the resulting data, as well as periodic access to the exact same area of the pipe surface for reevaluation.

Additionally, corrosion monitoring techniques can include the boring from the outside metal surface a plurality of holes which will be corroded through prior to that estimated to be the final rupture point. When the remaining wall thickness of the bores has been breeched by corrosion, such holes are at various locations throughout the test subject provide a "telltale" indication in a form of a small and controllable leak thereby signaling the need for repair or replacement prior to a greater, and potentially catastrophic failure. Once a telltale hole is penetrated, it must be repaired. Future telltale holes cannot be located at previous sites.

An alternative method of measurement of corrosion has been to bore completely through the metal wall in order to provide access for a gauging or inspection device and temporarily plugging the test opening between test cycles.

In a more complicated arrangement a plurality of bores are set for preselected depths from the outer surface of the system in the actual metal of a system past a point at which failure is expected to occur (borings are made closer to the interior of the test surface). Radioactive tracer elements are placed in the bores and sealed in place. Corrosion of the interior metal surface, once it penetrates through to the bore, releases the tracer element into the fluid flow for electronic detection at a central location. Such testing would be environmentally difficult to pursue today.

Another system relates to a device comprising both a pipe and a telltale plug, whereby the fluid corrodes through the pipe material to reach the plug and produce a visual leak. Telltale plug serves as a conduit for the fluid only. It requires modification to the piping system by boring, or taping into the pipe, exposing the pipe system to an additional threat. It cannot be used in thin wall applications and exposes individuals to the hazard of fluid leakage and contamination.

The prior art devices known use the corrosive break through of the piping system itself rather than a surface of the plug. The composition of the device determines the type of metal corrosion to monitor. Also the prior art intended to monitor the increasing corrosivity of a fluid before the point it will damage an internal combustion engine or the like, rather than monitor the actual amount of metal loss.

SUMMARY OF THE INVENTION

An object of the present invention is to provide an indication or signal to owners and operators of any pipe, tank, pressure vessel, reaction vessel or other fluid containment or transmission systems that a specific and predetermined amount of wear at various points of the internal metal surface has occurred.

Another object of the present invention to indicate in either one large step, identified in some measure or thickness, or in multiple smaller steps, also measured in some measure or thickness, the rate of advancement of interior corrosion which is occurring.

Still another object of the present invention is to set or predetermine the allowable thickness of metal to be corroded and then provide an indication of when that thickness limit has been exceeded.

Still a further object of the present invention is a disposable, self contained, stand alone device not requiring any further evaluation, energy, information processing, handling, maintenance or testing in order to produce an indication that the corrosion condition has deteriorated the subject metal past a set limit.

The monitor of the present invention is intended to serve similarly to an old style screw type electrical fuse, whereby an indication at the front of the device signals a problem condition.

Another object of the present invention is to provide a corrosion monitor which is intended for use in a more aggressive corrosive environment where corrosion activity is always present and expected to occur rather than in the type of environment in which prior monitor devices are employed.

Still a further object of the present invention is to provide a corrosion monitor that can be tailored to meet any varying monitoring needs due to the various types of piping and material carrying systems operating under even more varying environmental conditions.

Still a further object of the present invention is to provide a corrosion monitor that can be predetermined in its starting wall thickness to provide warning at any wall loss interval, monitoring short or long steps in corrosion loss depending upon desire.

A feature of the present invention is the provision of a self-contained, disposable corrosion monitor for a fluid containing system comprising a plug insertable into a system containing a fluid, the plug indicating a preselected amount of loss of the predetermined metal on the inner wall of the system due to corrosive action of the fluid on the inner wall of the system, the plug including a solid monitoring wall of predetermined metal having a thickness equal to the preselected amount of loss and one surface exposed to the fluid when the plug is inserted into the system at the same level as the inner wall of the system, an enclosed cavity associated with the other surface of the monitoring wall, and a substance disposed within the enclosed cavity reacting with the fluid penetrating the monitoring wall to indicate when the fluid has penetrated the monitoring wall, and, hence, that the preselected amount of loss of the metal in the inner wall of the system has occurred.

BRIEF DESCRIPTION OF THE DRAWING

Above-mentioned and other features and objects of the present invention will become more apparent by reference to the following description taken in conjunction with the accompanying drawing, in which:

FIG. 1 is a cross-sectional view illustrating the self-contained, disposable corrosion monitor for a fluid containing system in accordance with the principles of the present invention; and FIG. 2 is a view taken along line 2—2 of FIG. 1.

DESCRIPTION OF THE PREFERRED EMBODIMENTS

Referring to FIGS. 1 and 2, the self-contained, disposable corrosion monitor for a fluid containing system in accordance with the principles of the present invention includes a plug 1 insertable into a fluid containing system 2 manufactured from a predetermined metal including a fluid 3. The plug 1 is to indicate a preselected amount of loss of the predetermined metal of the system 2 on the inner wall 4 of the system 2 due to corrosive action of the fluid 3 on the inner wall 4.

Plug 1 includes a wall 5 of the predetermined metal of the system 2 having a thickness 0 equal to the preselected amount of loss of the predetermined metal on the inner wall 4. Wall 5 has one surface 6 exposed to fluid 3 when the plug 1 is inserted into the system 2 with surface 6 being the same level as the inner wall 4. A cavity 7 is associated with the other surface 8 of the wall 5. An indicator means 9 is associated with the cavity 7 to indicate when fluid 3 has penetrated wall 5 and, hence, that the preselected loss of the predetermined metal on inner surface 4 of system 2 has occurred.

The indicator 9 is a visual indicator in the form of a transparent member 10 disposed in cavity 7 remote from wall 5 to enable viewing fluid 3 in cavity 7 after wall 5 is penetrated by fluid 3. Plug 1 adjacent the transparent member 10 has a hexagonal configuration 11 as shown in FIG. 2 to enable threading the plug 1 into the system 2 for monitoring purposes.

To enhance the visual indication, a substance 12, such as a desiccant, is disposed in cavity 7 to change color when the fluid 3 penetrates wall 5 thereby illustrating or providing a visual indication of the penetration of wall 5.

Cavity 7 includes a first elongated portion 13 disposed adjacent to and parallel to the other surface 8 of wall 5 and at least a second elongated portion 14 disposed substantially perpendicular to the first longitudinal portion 13 extending from the first longitudinal portion 13 to the indicator means 9. The second longitudinal portion 14 may include a step bore arrangement as illustrated in FIG. 1, or may be of the same diameter as step section 15 adjacent the visual indicator 9.

The advantages of the present corrosion monitor as above described are numerous. The monitor of the present invention provides an immediate indication when the test wall 5 thickness has been corroded away. That indication may be provided by a visual change in color as viewed through transparent inspection port 10. The monitor is self-contained, stand alone corrosion monitor, requiring no laboratory examination or other physical testing either prior to or following the completion of its test cycle. Knowing its initial wall thickness 0 and time it has been in service, corrosion rate MPY can be easily calculated upon a formula of thickness 0 in inches divided by time in years.

The corrosion monitor provides the option of monitoring of corrosion loss over a small or large wall thickness dimension as is determined by the user. By selecting smaller testing wall thickness values, the user is enabled to monitor corrosion progress in shorter intervals, and thereby take any necessary action to reduce the fluids corrosive effect.

The monitor of the present invention may be used to monitor more aggressive forms of underdeposit corrosion caused by the build up of organic materials and particles on the metal surface. Such corrosion is not typically measured by corrosion coupons and other monitoring devices, since they are regularly taken out of service for cleaning, testing, evaluation or recalibration.

The present invention of the monitor may be easily removed from service and the test port replaced with another unit of same or different corrosion threshold or thickness 0.

The monitor of the present invention is extremely economical in comparison to all other corrosion monitoring devices and instrumentation, thereby extending corrosion monitoring protection further throughout any testing location or service application.

No permanent boring of the metal inner surface of the fluid containing system is necessary and the monitor contains no hazardous material or reactive substances.

There is no form of maintenance to the monitor of the present invention and the product has an indefinite operating surface life limited only by the corrosive action on its test surface 6.

The monitor of the present invention can monitor the corrosion due to exposure of a metal surface to moisture or a gas rather than just a liquid alone. Also the monitor of this present invention may be used in applications where there is little or no fluid flow or little or no fluid pressure. The monitor of the present invention may also be used to monitor the corrosive effect against any metal caused by any fluid and may be used in any physical position.

The monitor of the present invention will allow the measurement of different forms of corrosion and will allow operating personnel to measure different levels of corrosion cooexisting within the same piping system.

There are a number of different forms of corrosion which may attack a metal surface these forms are as follows.

General corrosion is the well distributed and low level attack against the entire metal surface with little or no localized penetration. It is the least damaging of all forms of corrosion. Generalized corrosion usually occurs in environments in which the corrosion rate is inherently low or well controlled. It is the only form of corrosion whereby weight loss or metal loss data (such as corrosion coupons) can be used to accurately estimate corrosion rates and future life expectancy.

Pitting corrosion is a localized, deep penetration of the metal surface with little general corrosion in the surrounding areas. Due to surface deposits, electrical imbalance or other mechanisms, all corrosion factors attack a select number of individual sites. In some cases pitting is extended throughout the entire metal surface, giving it an irregular or rough surface profile. In other instances, pits are concentrated in specific areas, leaving the majority of metal in like new condition. Pitting is the most common form of corrosion found where there are incomplete chemical protective films, and insulating or barrier deposits of dirt, iron oxide, organic or other foreign substances in the fluid system. Pitting corrosion may include, crevice corrosion, water line attack, deposit attack, impingement or erosion corrosion attack and concentration-cell corrosion.

Galvanic corrosion is an aggressive and localized form of corrosion due to electrochemical reaction generally between two or more dissimilar metals in a conductive environment. The more electro-negative material (the anode) is attacked by the more electro-positive material (the cathode). The most common example of such corrosion activity, widely found throughout high volume air conditioning operations, is the direct connection of brass valves to carbon steel pipe, or between copper and steel pipe. Carbon steel pipe, without the protection of galvanic insulator, will show the highest rate of corrosion in such conditions, developing over many years. While galvanic corrosion is generally assumed to involve only dissimilar metals, millivolt potentials can actually be measured between similar metals under certain conditions. New steel pipe installed during a repair or renovation is often more electro-negative than older existing pipe, and, therefore, may suffer from some degree of galvanic attack.

MIC corrosion is probably the most severe and threatening form of corrosion to high volume air conditioning piping systems caused by the presence of various microbiological agents under specific environmental conditions, in some cases resulting in advanced and widespread failure of entire piping system within a few years. Microbiological induced corrosion (MIC) produces large and deep pits due to its utilization of iron as an energy source (often as an alternative option), and the production of strongly corrosive metabolic by-products, such as sulfuric acid, which further assists the microorganism in dissolving the metal.

Erosion corrosion is the gradual deterioration of a metal surface due to mechanical wear and abrasion. Attributed to entrapped air bubbles, suspended matter and particles under a flow rate of sufficient velocity. Similar to impingement attack and primarily found at elbows and T's. Softer metals, such as copper and brass, are inherently more susceptible to erosion corrosion. High pressure steam frequently contributes to the erosion of carbon steel.

All of the prior art mechanisms for monitoring corrosion only address the corrosivity of the fluid, and not the actual thickness loss of metal. Therefore, corrosion loss based upon any of the above corrosion mechanisms other than generalized corrosion will not be measured by the prior art. Many of the most destructive forms of corrosion mechanisms, in fact, only develop once foreign dirt, bacteria and debris enter the circulated system and deposit out. Such is not the case of automotive cooling systems, the intended application of most of the prior art, where it is a closed system from the atmosphere and the antifreeze liquid is inherently clean.

For the application intended for the monitor of the present invention, the high volume air conditioning cooling towers and other open circulating systems, input of dirt, bacteria and debris is a constant occurrence bringing into the system foreign elements which often produce different corrosion scenarios. The monitor of the present invention will measure other forms of corrosion identified above dependent upon its placement.

An important feature of the monitor of the present invention is the ability to move the device to areas, which, based upon prior knowledge, an understanding of the system or previous problems, where greater corrosion is likely to occur. Unlike prior art which is in a fixed location, the monitor of the subject invention can be utilized anywhere, and requires no electrical hookup or further testing or analysis. As mentioned, the monitor of subject invention is the equivalent of an electrical fuse monitoring an excess amount of current, namely, a fluid fuse which monitors an excess amount of corrosion.

Inserting the plug 1 into a dead ended section of a pipe will provide an indication of corrosion due to the buildup of dirt and biological material, and, therefore, MIC and pitting corrosion. Inserting the plug 1 into a brass valve will add the corrosion activity due to galvanic action, and will indicate a greater amount of attack at a carbon steel test plug due to the more aggressive flow of A electrons from the brass valve to the steel. This would simulate the corrosion existing at other threaded brass to carbon steel connections prevalent to most piping systems and typically the first to fail.

Placement of the test plug at different points within the piping system, or fluid containing system, will also provide varying indications of corrosion. Placement of plug 1 at vertically oriented piping will likely show lower rates of corrosion, since foreign deposits can rarely settle and adhere to vertical piping. Horizontal sections will show the opposite. Placement at the outer radius of an elbow will add the corrosion effect of dirt or air on the surface 6 of plug 1, measuring the combined effect of corrosion itself as well as metal loss due to physical erosion and the inertia of the particulates. Placement of the plug 1 at smaller pipelines will likely show the higher corrosion rates present in such lines due to lower flow rates, the recognized phenomena that anti-corrosion chemicals often perform worse at low flow conditions. Conversely, placement of the plug 1 in larger main riser piping having higher flow rates will likely show lower corrosion rates there. The placement of plug 1 at roof level locations will document the higher rates of corrosion usually present when a fluid system is drained of treated water and left under moist conditions.

Overall, it is a great benefit of the monitor of the present invention to allow a building or piping operator to determine corrosion rates at his own areas of concern. Most important, the self-contained monitor of the present invention will allow an engineer or building operator to monitor or check the different forms of corrosion which typically coexist to different degrees of severity within any fluid containing system.

A key feature of this corrosion monitor, already stated in the patent application, is the fact that the client or end user can both define the amount of corrosion progress they are interested in measuring, and that they can simultaneously measure different forms of corrosion, i.e. galvanic, erosion, etc., by placing the device at the appropriate locations within the fluid environment. Contrasted again to corrosion coupons which record metal loss over a fixed period of time, this monitor provides a fixed material thickness to corrode and notifies the user of the time when corrosion has worn that metal away—an extremely important differentiation.

A major corrosion problem, in fact, exists at the threaded ends of a piping system—this due to the initial loss of material upon threading—due to corrosion which occurs between the voids of the threads, and due to the galvanic activity which commonly exists at the threaded joint. Failures at threaded connections, in fact, lead all other types of piping failures.

As we know, this monitor allows the user to define the thickness of the forward or fluid immersed end of the test plug, and, therefore, the amount of corrosion to be monitored. That is done by modifying, during the manufacturing process, the interior dimension parallel to the forward edge of the plug in greatest contact with the fluid. In addition to modifying this dimension, the design of this monitor also allows the diameter of the hollow interior to be modified as well.

Producing a larger hollow core diameter in relation to the overall plug diameter will reduce the dimension between the actual exterior pipe thread innermost grooves and that hollow interior area - thereby allowing the monitoring of thread based corrosion by the same previously described visual indication once the side or threaded wall surface of the monitor, that surface perpendicular to the forward edge of the device, is penetrated by the corroding liquid.

While I have described above the principles of my invention with specific apparatus, it is to be clearly understood that this description is made only by way of example and not as a limitation to the scope of my invention as set forth in the objects thereof and in the accompanying claims.

I claim:

1. A self-contained, disposable corrosion monitor for a fluid containing system comprising:
    a plug insertable into a fluid containing system, said plug indicating a preselected amount of loss of metal on an inner wall of said fluid containing system due to corrosive action of said fluid on said inner wall of said fluid containing system,
    said plug including
        a solid monitoring wall of a predetermined metal having a thickness equal to said preselected amount of loss and one surface exposed to said fluid when said plug is inserted into said fluid containing system at the same level as said inner wall of said fluid containing system,
        an enclosed cavity associated with the other surface of said solid monitoring wall, and
        a substance disposed within said enclosed cavity reacting with said fluid penetrating said solid monitoring wall to indicate when said fluid has penetrated said solid monitoring wall and, hence, that said preselected amount of loss of said metal on said inner wall of said fluid containing system has occurred.

2. A corrosion monitor according to claim 1, further includes
    a transparent member disposed in said enclosed cavity remote from said solid monitoring wall to enable viewing said fluid and said substance in said cavity after said solid monitoring wall is penetrated by said fluid.

3. A corrosion monitor according to claim 2, wherein said substance changes color when said fluid penetrates said solid monitoring wall, said color change being viewed through said transparent member.

4. A corrosion monitor according to claim 1, wherein said enclosed cavity includes
    a first elongated portion disposed adjacent to and parallel to said other surface of said solid monitoring wall, and
    at least a second elongated portion disposed substantially perpendicular to and extending outward from said first elongated portion.

5. A corrosion monitor according to claim 4, further including
    a transparent member disposed in said second elongated portion remote from said first elongated portion to enable viewing said fluid and said substance in at least said first elongated portion after said solid monitoring wal is penetrated by said fluid.

6. A corrosion monitor according to claim 5, wherein said substance is disposed within at least said first elongated portion, said substance changing color when said fluid penetrates said solid monitoring wall, said changing color being viewed through said transparent member.

* * * * *